(12) United States Patent
Bakker-Arkema et al.

(10) Patent No.: US 6,645,959 B1
(45) Date of Patent: Nov. 11, 2003

(54) METHOD FOR TREATING POSTOPERATIVE ILEUS

(75) Inventors: Rebecca Guggemos Bakker-Arkema, Ann Arbor, MI (US); Milton Lethan Pressler, Saline, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/111,274

(22) PCT Filed: Nov. 8, 2000

(86) PCT No.: PCT/US00/30768

§ 371 (c)(1),
(2), (4) Date: Apr. 19, 2002

(87) PCT Pub. No.: WO01/54698

PCT Pub. Date: Aug. 2, 2001

Related U.S. Application Data

(60) Provisional application No. 60/178,208, filed on Jan. 26, 2000.

(51) Int. Cl.[7] .................. A61K 31/55; A61K 31/34; A61K 31/5517; A61K 31/27
(52) U.S. Cl. .................. 514/215; 514/200; 514/481; 514/471
(58) Field of Search ................ 514/220, 215, 514/481

(56) References Cited

FOREIGN PATENT DOCUMENTS

| | | |
|---|---|---|
| EP | 0 709 386 A1 | 5/1996 |
| JP | 8-231403 | 10/1996 |
| WO | WO 99/24051 | 5/1999 |
| WO | WO 99/38533 | 8/1999 |
| WO | WO 99/51242 | 10/1999 |
| WO | WO 99/65525 | 12/1999 |

OTHER PUBLICATIONS

PCT International Search Report for PCT/US00/30768.

*Primary Examiner*—Zohreh Fay
*Assistant Examiner*—Brian Yong S. Kwon
(74) *Attorney, Agent, or Firm*—Charles W. Ashbrook

(57) ABSTRACT

This invention is a method for preventing or treating postoperative ileus comprising administering a vasopressin antagonist such as a compound of Formula (1), where $R^1$, $R^2$, and $R^3$ include hydrogen, halo, alkyl, and alkoxy; R and $R^5$ are hydrogen or alkyl; $R^4$ is hydrogen, phenyl, or substituted phenyl, and pharmaceutically acceptable salts thereof.

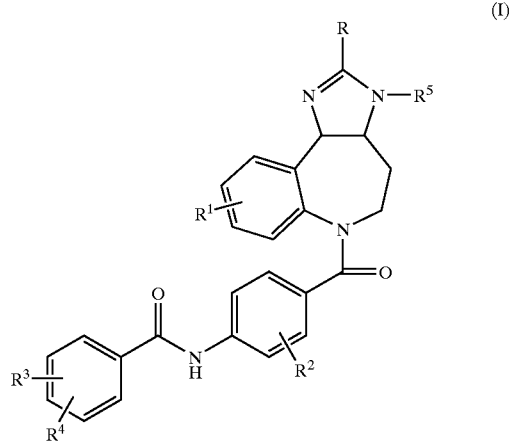

1 Claim, No Drawings

METHOD FOR TREATING POSTOPERATIVE ILEUS

This application claims the benefit of U. S. Provisional Application No. 60/178208 filed Jan. 26, 2000.

FIELD OF THE INVENTION

This invention relates to a method for preventing or treating postoperative ileus by administering a composition which inhibits the action of vasopressin and/or other substances which bind to vasopressin receptors.

BACKGROUND OF THE INVENTION

Gastric and colonic motility disturbances are quite common after intra-abdominal surgery. The small bowel is largely unaffected, and motility and absorption are normal within a few hours after operation. Stomach emptying is usually impaired for about 24 hours, but the colon may remain inert for 48 to 72 hours or more. This condition is known as postoperative ileus and its occurrence not only prolongs hospitalization, but also fosters postoperative complications, especially aspiration pneumonia. Symptoms and signs include abdominal distension, vomiting, obstipation, and cramps. Auscultation reveals a silent abdomen and minimum peristalsis. X-rays show gaseous distension of isolated segments of both small and large bowel. Treatment usually involves continuous nasogastric suction, nothing by mouth, intravenous (IV) fluids and electrolytes, and a minimal amount of sedatives. Sometimes colonic ileus can be relieved by colonoscopic decompression, but rarely cecostomy is required. Ileus persisting for a fill week or longer may be caused by a mechanical obstruction.

Studies using isolated canine jejunal segments have shown that following exposure to vasopressin, the jejunum becomes atonic with intraluminal pooling of perfusate. Transit time was prolonged, and intestinal absorption of water was decreased. Radionuclide imaging confirmed loss of intestinal motility. The studies concluded that the high plasma levels of vasopressin which are known to follow laparotomy may be a factor in the development of postoperative ileus.

Studies using monkeys who had strain gauge transducers implanted in the colon showed that the frequency of basal colonic contractions was reduced with increasing doses of vasopressin. The results suggest that the physiological concentrations of serum vasopressin present postoperatively may transiently inhibit colon contractions.

Vasopressin, also known as antidiuretic hormone (ADH), is a peptide synthesized in the magnocellular neurosecretory cells of the paraventricular and supraoptic nuclei of the hypothalamus, and is stored in the posterior pituitary. Vasopressin is released into the circulation in response to an increase in plasma osmolality (mediated by osmoreceptors) or a decrease in plasma volume or blood pressure (mediated by baroreceptors). However, there are other stimuli for vasopressin release, including circulating norepinephrine, angiotensin II, pain, hypoxia, nausea and vomiting, and fever. During laparoscopy a decrease in circulating plasma volume, pneumoperitoneum, and a neuronal impulse from the surgical site may result in raised levels of circulating arginine vasopressin (AVP). This rise in AVP may in turn lead to increased splachnic vascular resistance and mesenteric vasoconstriction, reduction of superior mesenteric artery blood flow and mesenteric microcirculation reduction ineffective perfusion pressure, and finally, splachnic ischemia. Splachnic ischemia, in turn, can cause an increase in splachnic free redical formation, a decrease in gut metabolic activity, and bacterial translocation—factors resulting in paralytic ileus.

The cellular effects of vasopressin are mediated by interaction of the hormone with two principal types of receptors, $V_1$ and $V_2$. $V_1$ receptors have been subclassified further as $V_{1a}$ and $V_{1b}$. The $V_{1a}$ receptor is the most widespread subtype and is found in vascular smooth muscle, myometrium, the bladder, adipocytes, hepatocytes, platelets, renal medullary interstitial cells, vasa recta in the renal microcirculation, epithelial cells in the renal cortical collecting duct, spleen, testis, and in many CNS tissues. Only the adrenohypophysis is known to contain $V_{1b}$ receptors. The $V_2$ receptors are predominantly located in principal cells of the renal collecting duct system.

Vasopressin is one of the most potent vasoconstrictors known ($V_1$ receptor mediated) and the vasopressin response to hypovolemia or hypotension serves as a mechanism to stave off cardiovascular collapse during periods of severe blood loss and/or hypotension (Laszlo, et al., *Pharmacol Rev.*, 1991;43:73–108). Vascular smooth muscle in the skin, skeletal muscle, fat, pancreas, and thyroid gland appear most sensitive, with significant vasoconstriction also occurring in the coronary vessels, brain, and gastrointestinal tract. It has been shown (Thibonnier, 1988) that administration of a peptide $V_1$ receptor antagonist improves hemodynamic function in patients with increased peripheral resistance due to heart failure.

We have discovered that compounds which inhibit binding of vasopressin to vasopressin receptors in the gastrointestinal tract can significantly reduce the incidence of postoperative ileus.

SUMMARY OF THE INVENTION

This invention provides a method for treating or preventing postoperative ileus comprising administering to a patient an effective amount of a vasopressin antagonist. The vasopressin antagonist to be employed is any chemical compound that is effective in inhibiting the biological activity of any known vasopressin or antidiuretic hormone. Numerous compounds are known to be vasopressin antagonists, and any of such compounds can be utilized in the method of this invention.

In a preferred embodiment, the vasopressin antagonist to be utilized is a condensed benzazepine such as those described in U.S. Pat. No. 5,723,606, incorporated herein by reference. In a further preferred embodiment, the vasopressin antagonist is an imidazo benzazepine of the Formula I:

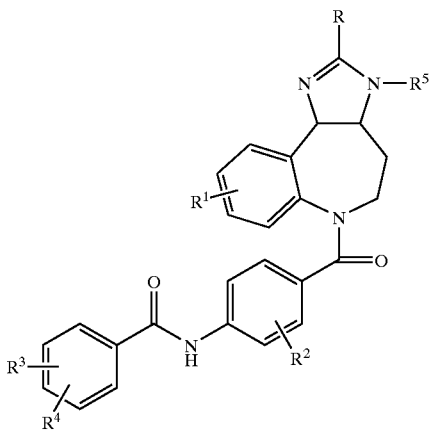

wherein:
R and $R^5$ are independently hydrogen or lower alkyl;
$R^1$, $R^2$, and $R^3$ independently are hydrogen, halo, lower alkyl, lower alkoxy, amino, alkylamino, or dialkylamino; and
$R^4$ is hydrogen, phenyl or substituted phenyl, and pharmaceutically acceptable salts thereof.

An especially preferred vasopressin antagonist to be used in accordance with this invention is conivaptan, which is N-[4-(2-methyl-4,5,6- tetrahydromidazo [4,5-d][1] benzazepin-6-ylcarbonyl)phenyl]biphenyl-2-carboxamide hydrochloride. Conivaptan is also referred to as YM087 and CI-1025, and has the structural Formula II below:

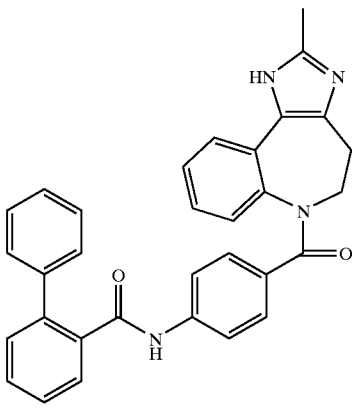

Other vasopressin antagonists that can be employed according to this invention include the benzoheterocyclic compounds described in U.S. Pat. No. 5,258,510, incorporated herein by reference. Preferred compounds from this class to be used herein include the following:

5-Dimethylamino-1-[4-(2-methylbenzoylamino)-benzoyl]-2,3,4,5-tetrahydro-1H-benzazepine;

5-Dimethylamino-1-[2-chloro-4-(2-methylbenzoylamino) benzoyl]-2,3,4,5-tetrahydro-1H-benzazepine;

5-Methylamino-1-[2-chloro-4-(2-methylbenzoylamino) benzoyl]-2,3,4,5-tetrahydro-1H-benzazepine;

5-Cyclopropylamino-1-[2-chloro-4-(2-methylbenzoylamino) benzoxyl]-2,3,4,5-tetrahydro 5-Cyclopropylamino-1-[2-chloro-4-(2-chlorobenzoylamino) benzoxyl]-2,3,4,5-tetrahydro-1H-benzazepine;

5-Dimethylamino-1-[2-methyl-4-(2-methylbenzoylamino) benzoyl]-2,3,4,5-tetrahydro-1H-benzazepine;

5-Dimethylamino-1-[2-methoxy4-(2-methylbenzoylamino) benzoyl]-1,2,3,4-tetrahydroquinoline;

7-Chloro-5-methylamino-1 -[4-(2-methylbenzoylamino) benzoxyl]-2,3,4,5-tetrahydro-1H-benzazepine; and 7-Chloro-5-methylamino-1-[4-(2-chlorobenzoylamino) benzoxyl]-2,3,4,5-tetrahydro-1H-benzazepine.

DETAILED DESCRIPTION OF THE INVENTION

In Formula I above, R and $R^5$ are hydrogen or lower alkyl. The term "lower alkyl" means a straight or branched carbon chain having from 1 to 6 carbon atoms. Typical lower alkyl groups include methyl, ethyl, isopropyl, n-butyl, neopentyl, and 1,1-dimethylbutyl.

"Halo" is a halogen atom such as fluoro, chloro, bromo, and iodo. "Lower alkoxy" means the $C_1$–$C_6$ alkyl groups mentioned above linked through an oxygen atom. Examples of lower alkoxy include methoxy, ethoxy, isopropoxy, sec-pentyloxy, and n-hexyloxy.

The term "alkylamino" means an amino group ($—NH_2$) substituted with one $C_1$–$C_6$ alkyl group. Typical alkylamino groups include methylamino, isopropylamino, n-pentylamino, and tert-butylamino. "Dialkylamino" means an amino group having two $C_1$–$C_6$ alkyl groups, for example, dimethylamino, N-ethyl-N-hexylamino, diisopropylamino, and N-butyl-N-methylamino.

$R^4$ is hydrogen, phenyl, or substituted phenyl. The term "substituted phenyl" means a phenyl group substituted with 1, 2, or 3 groups selected from lower alkyl, lower alkoxy, halo, amino, alkylamino, and dialkylamino, as those terms are defined above.

Any vasopressin antagonist can be administered to a patient to prevent or treat postoperative ileus according to this invention. The term "vasopressin antagonist," as is used herein, means any compound which can bind to either the vasopressin receptor site or to vasopressin itself in a manner to prevent normal vasopressin activity. The term "patient" and "mammal" is used herein to mean an individual, including a human or animal, experiencing symptoms of postoperative ileus or an individual prior to abdominal surgery who, following surgery, has the potential to experience postoperative ileus. "Abdominal surgery" means any invasion of the mammal that reaches below the chest and above the knees. The term "effective amount" is used herein to mean a concentration of compound which, if administered, would prevent, reduce, or stop the symptoms or physical occurrence of postoperative ileus. Typical "effective amounts" are about 1 mg/kg to about 100 mg/kg. Preclinical pharmacologic studies have demonstrated potent binding of YM087 (conivaptan) to vasopressin receptors and antagonism of the vascular and renal effects of vasopressin. YM087 has high affinity for $V_{1a}$ and $V_2$ receptors with pKi (negative log of the binding inhibition constant) of 8.20 for human $V_{1a}$ receptors, and 8.95 for human $V_2$ receptors expressed in COS-1 cells.

In a preferred embodiment, a vasopressin antagonist is administered to a patient prior to a scheduled abdominal surgery, for example, from 1 to 6 hours prior to surgery, or upon postoperative transfer to the recovery room or intensive care unit in order to prevent or diminish the symptoms or signs of postoperative ileus.

The following detailed Examples illustrate the present invention. While the Examples describe data relating to the use of conivaptan as a preferred embodiment, the invention enhances the use of any vasopressin antagonist.

EXAMPLE 1

Conivaptan (YM087)

Clinical Pharmacology

YM087 given orally to rats antagonizes the AVP-induced pressor response ($V_1A$ antagonism) in a dose-related manner, with the dose that reduced the AVP response by 50% ($ID_{50}$) being 0.32 mg/kg. The $ID_{50}$ for a similar experiment using IV YM087 in dogs was 0.026 mg/kg. In conscious dogs, oral YM087 (0.03 to 0.3 mg/kg) increased urinary output ($V_2$ antagonism) and reduced urinary osmolality (from 1500 to <100 mOsm/kg $H_2O$) in a dose-related manner. Unlike furosemide, YM087 has little or no effect on urinary sodium (Na) or potassium (K) excretion. In dogs with heart failure induced by rapid right ventricular pacing, IV administration of YM087 (0.1 mg/kg) significantly improved the depressed cardiac function and produced a water diuresis.

Oral absorption of YM087 is rapid (peak concentrations reached between 0.5 to 1 hour in the rat and dog, respectively) and occurs predominantly in the small intestine. There is a marked food effect with absorption reduced by >50% in dogs after a meal. The elimination half-life is 1 hour in rats and 2 hours in dogs. Mass balance studies show the majority of radioactive tracer excreted in the feces.

The preclinical toxicologic potential of YM087 has been extensively evaluated, and all findings were evaluated for relevance to human risk assessment and impact on clinical trial design. Findings of potential concern were bone marrow changes in dogs and effects on fertility in rats.

Histopathologic changes in bone marrow were observed in both 2- and 13-week oral studies in dogs with systemic exposures 28- to 87-fold higher than the maximum anticipated human exposure. Decreased peripheral erythrocyte, leukocyte, and/or platelet counts occurred in affected dogs in the 13-week study. Bone marrow and peripheral blood changes were reversible.

YM087 did not affect reproductive performance of male rats. In the 13-week repeated oral dose study in rats, more females at 10 mg/kg were in diestrus or proestrus and fewer were in estrus than in controls, and uterine weights were decreased at all doses; associated systemic exposures were 0.06- to 3.2-fold the maximum anticipated human exposure. In the female fertility study in rats, reduced fertility index, increased implantation loss, and decreased live fetuses were observed in females given 100 mg/kg orally for 2 weeks prior to mating with untreated males. Effects on estrous cycle and fertility in female rats may be related to alterations in serum hormone levels resulting from pharmacologic activity of YM087. YM087 was not teratogenic in rats or rabbits.

Other drug-related effects, including diuresis and hepatocellular hypertrophy, were of less concern due to the nature of the effects or the high exposures at which the effects occurred compared to exposures anticipated in clinical trials.

YM087 was not mutagenic in bacteria and was not clastogenic in human lymphocytes in vitro or in bone marrow of rats. No toxicity was observed in 4-week IV studies with the glycerin formulation at maximum achievable doses, 2.5 mg/kg in rats and 2 mg/kg in dogs.

In summary, toxicological findings of potential concern for human risk assessment were reversible effects on bone marrow in dogs and reversible effects on estrus cycle and decreased fertility in rats. Findings in bone marrow were observed at exposures in excess of 23 times exposure expected in humans given the maximum dose of 120 mg once daily (QD), while effects on estrus cycle occurred at exposures from 0.05- to 3-fold the expected human exposure at 120 mg QD. Other drug-related findings in toxicology studies were considered secondary to pharmacologic activity or a functional adaptation to exposure to YM087.

YM087 has been given to approximately 250 healthy subjects who participated in a total of 15 Phase 1 studies (8 in Japan and 7 in Europe). Subjects taking oral medication received either a single dose of YM087 (dose range 0.2 through 120 mg) QD or 30 or 120 mg YM087 administered as a divided dose twice daily (BID). Subjects received YM087 as a single IV injection once daily over a dose range of 0.2 to 250 µg/kg or up to a maximum of 50 mg.

Inhibition of AVP-induced platelet aggregation (evidence of $V_{1A}$ antagonist activity) was seen among subjects who received YM087 at 20 mg/day orally or 2.5 mg IV. Total inhibition of AVP-induced dermal vasoconstriction was observed among subjects who received YM087 50 mg IV.

Normal subjects have demonstrated aquaretic action (evidence of $V_2$ receptor antagonism) accompanied by a decrease in urine osmolarity starting at 15 mg oral or 50 µg/kg IV. At higher doses aquaretic effects were more pronounced, and at 120 mg QD or 60 mg BID given orally or 50 mg given IV, were considered too uncomfortable in normal subjects to be tolerable. YM087 at IV doses up to 250 µg/kg and 50 mg/day increased urine production rate for up to 3 and 6 hours postdosing, respectively.

Under fasting conditions, YM087 is rapidly absorbed, time to maximum plasma concentration (tmax) being reached at around 1 hour. The mean oral bioavailability of a 60-mg dose is 44% under fasting conditions; bioavailability is decreased after intake with food. A high-fat breakfast reduced bioavailability of single 15- to 90-mg doses of YM087 to 43% to 59% of the fasted value, and peak plasma levels were reduced to 24% to 54% of the fasting value. Oral YM087 demonstrated a nonlinear pharmacokinetic profile. Repeated BID oral doses of YM087, 60 mg, result in unexpectedly high plasma levels after the second dose, possibly caused by reduced first-pass metabolism. YM087 displays 2 compartment pharmacokinetics with an elimination half-life of 4 to 5 hours.

Elderly subjects have a similar elimination half-life as healthy young volunteers.

The pharmacokinetics of orally administered YM087 (20 mg) were not affected when combined with either 0.5 mg IV digoxin or 25 mg oral captopril (each given as a single dose).

Safety

Among approximately 250 subjects treated, no major safety concerns were identified. One patient with severe congestive heart failure (CHF) who received YM087 80 mg/day for 4 days experienced a generalized tonic clonic seizure which the investigator could not exclude as related to study drug. The most frequent adverse events regardless of treatment association were mild or moderate thirst and mild headache. Other adverse events included flushes, a sensation of cold extremities, abdominal complaints, abnormal stools, syncope, dizziness, palpitations, and postural hypotension. Three subjects who received YM087 and one subject who received placebo developed minor reversible decreases in white blood cell count. No drug-related trend was observed in biochemical or hematological laboratory parameters. At higher doses, urinary osmolarity decreased and plasma osmolarity increased with or without an increase in plasma sodium. These observations were considered related to antagonism of $V_2$ receptors and not a safety concern. Vital signs (blood pressure and heart rate) were unaffected by YM087.

EXAMPLE 2

Treatment of Postoperative Ileus

Study Rationale

The following study can be employed to establish the clinical efficacy of vasopressin antagonists in diminishing postoperative ileus.

Patients who have had major abdominal surgery show dramatic rises in vasopressin (20–30 times). Dilutional hyponatremia (low plasma sodium), as a direct or indirect consequence of vasopressin release, is also very common after major abdominal surgery. There is reason to believe that following surgery vasopressin is released and binds to receptors in capillary beds which supply the gut. This binding results in gut ischemia and/or intestinal muscular contraction which restricts gut peristalsis and results in the symptoms defined as postoperative ileus. The prophylactic administration and/or early postoperative treatment using a vasopressin antagonist in patients undergoing abdominal surgery and are at risk for hyponatremia will thus relieve or eliminate postoperative ileus according to this invention.

Study Objectives

The objectives of this study are:

To assess the effect and pharmacodynamic actions of YM087 in patients at risk for postoperative ileus.

To determine the safety of giving YM087 to patients at risk for postoperative ileus.

Study Design

This is an open-label randomized study assessing the safety and efficacy of YM087 when given prophylactically or postsurgically to patients who are to undergo abdominal surgery and may be at risk for postoperative ileus or have already developed postoperative ileus. Patients will either be randomirzed prior to abdominal surgery or following the development of postoperative ileus. For those randomized prior to surgery, bowel x-rays will be taken immediately prior to surgery as well as a standard chemistry panel, serum and urine electrolytes. CI-1025 will be administered >30 minutes prior to induction of general anesthesia and surgery in the study group, and placebo will be administered to the control patients. Infusion of CI-1025 and/or matching placebo will be continued throughout surgery and for 24 hours postoperatively. Following surgery, clinical chemistry, blood and urine electrolyte values will be determined at 6-hour intervals for 4 days. For those randomized after the development of postoperative ileus, a bowel x-ray, clinical chemistry panel, serum and urine electrolytes will be taken prior to drug administration. Bowel x-rays will be taken daily for 4 days in both groups. Surgical complication rates, incidence and duration of ileus, and sodium changes will be assessed at the same 6-hour intervals for 4 days. Patients with plasma sodium values below 135 mmol/L will be classified as hyponatremic.

Study Population

Source and Number of Patients

Number of Patients: 10 to 20 study patients and 10 to 20 controls; 20 to 40 patients total Source: Patients who are scheduled to have major abdominal surgery Inclusion Criteria These criteria are mandatory and must be met to provide evaluable data.

Males or females 18 to 85 years of age

Females must be postmenopausal, surgically sterilized, or practicing a barrier method of birth control so that in the opinion of the investigator, they are not pregnant.

Exclusion Criteria

Breastfeeding or pregnant;

Signs of dehydration

Preoperative bowel obstruction or ileus

Significant renal impairment (serum creatinine >2.5 mg/dL or creatinine clearance <30 mL/min); or nephrotic syndrome;

Known urinary outflow obstruction (e.g., stenosis, stone, tumor, etc.);

Alanine aminotransferase (ALT) or aspartate aminotransferase (AST) >3 ×upper limit of normal (ULN) and/or bilirubin ≧2.5 mg/dL; or cirrhosis with ascites;

Uncontrolled hyper- or hypothyroidism;

Adrenal insufficiency (AM cortisol <7 μg/dL);

Serious hematological diseases (e.g., severe anemia, Hgb <10 g/dL; leukopenia, WBC <4000/μL);

Significant hypotension (SBP <95) or uncontrolled hypertension;

Concurrent enrollment in a chemotherapy or radiation regimen;

Unstable angina or acute myocardial infarction within 30 days of the screening visit;

Participation in another clinical trial of an investigational drug (including placebo) within the 30 days prior to screening for entry into the present study;

History of current or past use of illicit drugs or alcoholism unless abstinence can be documented for ≧6 months;

Other medical conditions, such as significant obstructive cardiac valvular disease and/or hypertrophic subaortic stenosis, obstructive lung disease, dementia, or significant abnormalities that the investigator feels may compromise the patient's safety or successful participation in the study; and Inability to understand and sign the Informed Consent to participate in this study.

Prohibited Drugs

The following medications may not be taken during this study:

Any antineoplastic agent;

Any medication known to cause leukopenia;

Nonsteroidal anti-inflammatory drugs, with the exception of low-dose aspirin (≦325 mg/day); and Smoking pattern should not be altered for the duration of the investigation, as smoking has been found to stimulate the secretion of AVP from the posterior pituitary gland. Patients must not smoke immediately prior to blood sampling.

Drugs metabolized exclusively by CYP3A4 pathway (simvastatin, atorvastatin >40 mg, lovastatin, astemazole, terfenidine, cisapride).

Allowable Medications

The dosage and regimen of any other chronic, permitted concurrent medications (e.g., hormone replacement therapy, hormone contraceptives, thyroid replacement therapy, or H2 antagonists) should be stabilized before the enrollment. Any medications prescribed chronically or intermittently during the study, or dose adjustments of these medications, must be reported.

Efficacy Assessments

Primary Efficacy Parameter

The primary efficacy measure is time to resumption of colonic motility over 72 hours postabdominal surgery.

Secondary Efficacy Parameter

Incidence of postoperative ileus on abdominal x-ray by a reader blinded to the study drug. Maintenance of a normal level of plasma sodium from 12 to 96 hours postabdominal surgery.

Safety Assessments

Adverse Event Reportinz

Observe and query each patient in a nonspecific fashion at each visit during the study for any new or continuing symptoms since the previous visit.

Serious Adverse Events

A serious adverse event is defined as any adverse event at any dose that results in any of the following outcomes:

Death;

Life-threatening condition;

Inpatient hospitalization or prolongation of existing hospitalization;

Persistent or significant disability/incapacity;

Congenital anomaly/birth defect; and

Medically significant event (includes laboratory abnormalities) as determined by attending medical practitioner.

Clinically Important Adverse Events

The following laboratory value abnormalities are considered clinically important:

Significant leukopenia (WBC <1500/$\mu$L) or neutropenia (neutrophil count <500/$\mu$L);

Severe volume loss of water and/or electrolytes resulting in dehydration or significant worsening of renal function (increase in BUN by $\geq$40 mg/dL or increase in serum creatinine by $\geq$1.5 mg/dL).

Adverse Event Follow-up

All serious and routine adverse events are noted and recorded, including the onset, duration, severity, relationship to the study drug, and ultimate management. Adverse events reported during the baseline and treatment phases, and up to 15 days after the cessation of treatment, should be recorded and followed until the adverse event has subsided and abnormal findings have returned to normal or stabilized. The sponsor/principal investigator will stop the study at any time if new knowledge is gained and:

Safety for all participating patients can no longer be guaranteed; and/or

The risk-benefit ratio is no longer favorable for the participating patients.

Safety Monitoring

Safety Parameters

During the study, patients should be carefully monitored for signs of volume gain or loss, such as:

Body weight increases or decreases of 3 kg or more in a 24-hour period; or

Systolic blood pressure $\leq$80 mm Hg and presyncopal symptoms.

Adjustments of fluid intake or diuretic dose may be made at the discretion of the investigator if clinically significant changes in the patient's weight occur. If the patient continues to experience safety concerns, he or she should be withdrawn from the study.

Physical Examination

A physical examination will be performed during the Screening Phase and will be repeated at the end of the study. Vital signs and abdominal exam will be recorded daily. Significant adverse changes will be recorded as adverse events.

Safety Profile

A safety profile, which will include blood pressure, heart rate, weight, and assessment of volume status will be recorded throughout the study.

Pharmacokinetic/Pharmacodynamic Analysis

CI-1025 plasma concentrations will be measured using a validated LC/MS/MS method in the positive ionization mode. Sensitivity, specificity, linearity, and reproducibility will be determined before analysis of samples.

Removal of Patients From the Study

Make every effort within the bounds of safety and patient choice to have each patient complete the study.

Study Completion

Each patient will end the study upon completion of all procedures up to and including all days of the Treatment Phase.

Study Medication

Description

YM087 for injection (2 mg) will be prepared by standard methods. Medication for this study will be dispensed according to a randomization code. All study medications should be stored in a secure, locked area. Inventory control of all study medications must be rigorously maintained throughout the duration of the study until all medication has been accounted for.

Data Analysis and Statistical Considerations

Power and Sample Size

This is an exploratory pilot study. Patient numbers are not based on considerations of power, but are thought to be adequate to provide preliminary assessment of the safety and tolerability of YM087.

For use in preventing or treating postoperative ileus according to this invention, the vasopressin antagonist will be formulated with common excipients for convenient administration to patients.

The compositions to be employed in the present invention can be prepared and administered in a wide variety of oral and parenteral dosage forms for treating and preventing post-operative ileus. The compounds can be administered by injection, that is, intravenously, intramuscularly, intracutaneously, subcutaneously, submucosally; intraductally, intraduodenally, or intraperitoneally. Also, the compounds can be administered by inhalation, for example, intranasally. Additionally, the compositions can be administered transdermally. It will be obvious to those skilled in the art that the following dosage forms may comprise as the active component, either a compound as a free base, acid, or a corresponding pharmaceutically acceptable salt of such compound. The active compound generally is present in a concentration of about 5% to about 95% by weight of the formulation.

For preparing pharmaceutical compositions from the compounds to be used in the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcelluose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of each active component in a unit-dose preparation may be varied or adjusted from 1 to 1000 mg, preferably 10 to 100 mg according to the particular application and the potency of the active component. The composition can, if desired, also contain other compatible therapeutic agents.

The following additional examples illustrate typical formulations that can be utilized in the invention.

EXAMPLE 3

Parenteral Formulation

YM087 conivaptan is dissolved in isotonic saline at a concentration of 5 mg/mL. The solution is injected IV 2 hours prior to abdominal surgery.

EXAMPLE 4

Tablet Formulation

| Ingredient | Amount (mg) |
| --- | --- |
| YM087 Conivaptan | 10 |
| Lactose | 50 |
| Cornstarch (for mix) | 20 |
| Cornstarch (paste) | 15 |
| Magnesium stearate (1%) | 5 |
| Total | 100 |

The vasopressin antagonist, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for treatment of postoperative ileus.

EXAMPLE 5

Preparation for Oral Solution

| Ingredient | Amount |
| --- | --- |
| CI-1025 | 10 mg |
| Sorbitol solution (70% N.F.) | 40 mL |
| Sodium benzoate | 20 mg |
| Saccharin | 5 mg |
| Red dye | 10 mg |
| Cherry flavor | 20 mg |
| Distilled water q.s. | 100 mL |

The sorbitol solution containing CI-1025 is added to 40 mL of distilled water. The saccharin, sodium benzoate, flavor, and dye are added and dissolved. The volume is adjusted to 100 mL with distilled water. Each milliliter of syrup contains 4 mg of CI-1025 (conivaptan).

What is claimed is:

1. A method for treating postoperative ileus in a mammal who has undergone an abdominal surgery comprising administering an effective amount of conivaptan.

* * * * *